US005723693A

United States Patent [19]

Hefner, Jr. et al.

[11] Patent Number: 5,723,693

[45] Date of Patent: Mar. 3, 1998

[54] PROCESS FOR PREPARING AND RECOVERING 4,4'-DIHYDROXY-ALPHA-ALKYLSTILBENE OR 4,4'-DIHYDROXY-ALPHA, ALPHA'DIALKYLSTILBENE

[75] Inventors: Robert E. Hefner, Jr.; David A. Carr, both of Lake Jackson, Tex.

[73] Assignee: The Dow Chemical Company, Midland, Mich.

[21] Appl. No.: 713,906

[22] Filed: Sep. 13, 1996

[51] Int. Cl.$^6$ ............................................. C07C 39/215
[52] U.S. Cl. ........................................ 568/729; 568/724
[58] Field of Search ............................ 568/724, 729

[56] References Cited

U.S. PATENT DOCUMENTS

| | | | |
|---|---|---|---|
| 2,623,908 | 12/1952 | Stoesser et al. | 260/619 |
| 2,812,364 | 11/1957 | Farnham et al. | 260/619 |
| 3,221,061 | 11/1965 | Grover et al. | 260/619 |
| 3,326,986 | 6/1967 | Dugan et al. | 260/619 |
| 5,059,721 | 10/1991 | Powell et al. | 568/724 |
| 5,198,591 | 3/1993 | Kiedik et al. | 568/727 |
| 5,288,926 | 2/1994 | Patrascu et al. | 568/727 |
| 5,414,150 | 5/1995 | Hefner, Jr. et al. | 568/729 |
| 5,463,091 | 10/1995 | Earls et al. | 549/560 |
| 5,475,155 | 12/1995 | Hefner, Jr. et al. | 568/727 |

FOREIGN PATENT DOCUMENTS 949668  2/1964  United Kingdom .

OTHER PUBLICATIONS

Harrison, L. T., Journal of the Chemical Society, Chemical Communications, p. 616 (1969).

Kawasaki, I. et al., Bulletin of the Chemical Society of Japan, vol. 44, pp. 1986–1987 (1971).

McOmie, J. F. W. et al., Tetrahedron, vol. 24, pp. 2289–2292 (1968).

Percec, V. et al., Mol. Cryst. Liq. Cryst., vol. 205, pp. 47–66 (1991).

Zaheer, S. H. et al., Journal of the Chemical Society, Part I, pp. 3360–3362 (1954).

US Patent Application entitled, "Process for the Preparation and Purification of 4,4'-Dihydroxy-Alpha-Substituted Stilbene" filed Feb. 29, 1996; Serial No. 08/608,807; Applicants: A. P. Haag et al.

*Primary Examiner*—José G. Dees
*Assistant Examiner*—Barbara Badio
*Attorney, Agent, or Firm*—Ann K. Galbraith

[57] ABSTRACT

A process for preparing a 4,4'-dihydroxy-alpha-alkylstilbene or 4,4'-dihydroxy-alpha,alpha'-dialkylstilbene which includes the steps of (A) reacting at a temperature of from −20° C. to 20° C. a mixture of: (1) at least one alpha-haloketone; (2) at least one compound containing one phenolic hydroxyl group or aromatic alkoxy group per molecule such that the mole ratio of phenolic hydroxyl group-containing or aromatic alkoxy group-containing compound (s):alpha-haloketone(s) is at least 0.1:1; and (3) either (a) at least one strong protonic acid or (b) at least one Lewis acid, or (c) any combination thereof; thereby forming a reaction product containing at least one halogen-containing bisphenol compound which, upon being dehydrohalogenated, forms a 4,4'-dihydroxy-alpha-alkylstilbene or 4,4'-dihydroxy-alpha, alpha'-dialkylstilbene; (B) reducing the acid content of the product resulting from step (A) to less than 10.000 ppm; (C) dehydrohalogenating the product obtained from step (B), thereby forming a dehydrohalogenated product containing 4,4'-dihydroxy-alpha-alkylstilbene or 4,4'-dihydroxy-alpha,alpha'-dialkylstilbene; (D) adding water to the product of step (C) in amounts sufficient to crystallize at least a portion of the, 4,4'-dihydroxy-alpha-alkylstilbene or 4,4'-dihydroxy-alpha,alpha'-dialkylstilbene and recovering the crystals and the remaining organic phase separately; (E) independently repeating steps (A), (B), and (C) to obtain a dehydrohalogenated product; (F) mixing at least a portion of organic phase obtained in step (D) with the product obtained in step (E); and (G) adding water to the mixture obtained in step (F) in amounts sufficient to crystallize at least a portion of the 4,4'-dihydroxy-alpha-alkylstilbene or 4,4'-dihydroxy-alpha,alpha'-dialkylstilbene and recovering the crystals.

20 Claims, 1 Drawing Sheet

FIG. 1

PROCESS FOR PREPARING AND RECOVERING 4,4'-DIHYDROXY-ALPHA-ALKYLSTILBENE OR 4,4'-DIHYDROXY-ALPHA, ALPHA'DIALKYLSTILBENE

BACKGROUND OF THE INVENTION

Processes for the preparation of 4,4'-dihydroxy-alpha-alkylstilbene or 4,4'-dihydroxy-alpha,alpha'-dialkylstilbenes are known and are described, for example, in S. H. Zaheer, et al., *Journal of the Chemical Society*, Part 3, pp. 3360–3362 (1954); "Synthesis and Characterization of Thermotropic Polyethers and Copolyethers Based on 4,4'-Dihydroxy-alpha-methylstilbene and Flexible Spacers Containing Odd Numbers of Methylene Units" by V. Percec, et al., *Mol. Cryst. Liq. Cryst.*, Vol. 205, pp. 47–66 (1991); J. I. de Jong, British Patent 949,668 (1964); U.S. Pat. No. 2,623,908 (1952); U.S. Pat. No. 3,221,061 (1965); German Patent 1,031,788 (1958); and U.S. Pat. No. 2,812,364 (1957). The compounds may be isolated from the reaction product by adding water to the reaction mixture, as described in U.S. Pat. No. 3,326,986 (1967). However, the organic portion of the remainder of the reaction mixture contains a substantial amount of the compounds in solution. Such compounds are difficult to extract or otherwise recover from the organic liquid in a manner which is relatively efficient and cost effective.

SUMMARY OF THE INVENTION

In one aspect, this invention is a process for preparing a 4,4'-dihydroxy-alpha-alkylstilbene or 4,4'-dihydroxy-alpha,alpha'-dialkylstilbene which comprises:

(A) reacting at a temperature of from −20° C. to 20° C. a mixture of:

(1) at least one alpha-haloketone;

(2) at least one compound containing one phenolic hydroxyl group or aromatic alkoxy group per molecule such that the mole ratio of phenolic hydroxyl group-containing or aromatic alkoxy group-containing compound(s):alpha-haloketone(s) is at least 0.1:1; and     (3) either (a) at least one strong protonic acid or (b) at least one Lewis acid, or (c) any combination thereof;

such that the mole ratio of phenolic hydroxyl group-containing or aromatic alkoxy group-containing compound(s):alpha-haloketone(s):strong protonic acid(s) or Lewis acid(s) or combination thereof is from 0.1:1:0.0026 to 20:1:8; thereby forming a reaction product containing at least one halogen-containing bisphenol compound which, upon being dehydrohalogenated, forms a 4,4'-dihydroxy-alpha-alkylstilbene or 4,4'-dihydroxy-alpha, alpha'-dialkylstilbene;

(B) reducing the acid content of the product resulting from step (A) to less than 10,000 ppm;

(C) dehydrohalogenating the product of step (B), thereby forming a dehydrohalogenated product containing 4,4'-dihydroxy-alpha-alkylstilbene or 4,4'-dihydroxy-alpha, alpha'-dialkylstilbene;

(D) adding water to the product of step (C) in amounts sufficient to crystallize at least a portion of the 4,4'-dihydroxy-alpha-alkylstilbene or 4,4'-dihydroxy-alpha, alpha'-dialkylstilbene and recovering the crystals and the remaining organic phase separately;

(E) independently repeating steps (A), (B), and (C) to obtain a dehydrohalogenated product;

(F) mixing at least a portion of the organic phase obtained in step (D) with the product of step (E); and (G) adding water to the mixture obtained in step (F) in amounts sufficient to crystallize at least a portion of the 4,4'-dihydroxy-alpha-alkylstilbene or 4,4'-dihydroxy-alpha, alpha'-dialkylstilbene and recovering the crystals.

In a second aspect, this invention is a process for preparing a 4,4'-dihydroxy-alpha-alkylstilbene or 4,4'-dihydroxy-alpha,alpha'-dialkylstilbene which comprises:

(A) reacting at a temperature of from −20° C. to 20° C. a mixture of:

(1) at least one alpha-haloketone;

(2) at least one compound containing one phenolic hydroxyl group or aromatic alkoxy group per molecule such that the mole ratio of phenolic hydroxyl group-containing or aromatic alkoxy group-containing compound(s):alpha-haloketone(s) is at least 0.1:1; and     (3) either (a) at least one strong protonic acid or (b) at least one Lewis acid, or (c) any combination thereof;

such that the mole ratio of phenolic hydroxyl group-containing or aromatic alkoxy group-containing compound(s):alpha-haloketone(s):strong protonic acid(s) or Lewis acid(s) or combination thereof is from 0.1:1:0.0026 to 20:1:8; thereby forming a reaction product containing at least one halogen-containing bisphenol compounds which, upon being dehydrohalogenated, forms a 4,4'-dihydroxy-alpha-alkylstilbene or 4,4'-dihydroxy-alpha, alpha'-dialkylstilbene;

(B) reducing the acid content of the product resulting from step (A) to less than 10,000 ppm;

(C) dehydrohalogenating the product obtained from step (B), thereby forming a dehydrohalogenated product containing 4,4'-dihydroxy-alpha-alkylstilbene or 4,4'-dihydroxy-alpha, alpha.alpha'-dialkylstilbene;

(D) adding water to the product of step (C) in amounts sufficient to crystallize at least a portion of the 4,4'-dihydroxy-alpha-alkylstilbene or 4,4'-dihydroxy-alpha, alpha'-dialkylstilbene;

(E) recovering the crystals and the remaining organic phase separately;

(F) independently repeating steps (A), (B), (C), and (D) to obtain an aqueous slurry containing crystallized 4,4'-dihydroxy-alpha-alkylstilbene or 4,4'-dihydroxy-alpha, alpha'-dialkylstilbene;

(G) mixing at least a portion of the organic phase obtained in step (D) with the slurry obtained in step (F) under conditions sufficient to crystallize at least a portion of the 4,4'-dihydroxy-alpha-alkylstilbene or 4,4'-dihydroxy-alpha, alpha'-dialkylstilbene present in the organic phase obtained in step (D); and recovering the crystals of 4,4'-dihydroxy-alpha-alkylstilbene or 4,4'-dihydroxy-alpha,alpha'-diaikylstilbene.

These processes provide a means by which 4,4'-dihydroxy-alpha-alkylstilbene or 4,4'-dihydroxy-alpha, alpha'-dialkylstilbene (hereafter collectively referred to as "dihydroxy alkylstilbenes") may be separated from a mixture of such compounds, starting materials used in their preparation, and other oligomeric species (such as dimers or trisphenols) typically present in the reaction product. During the crystallization step, the percentage of the compounds which crystallize is believed to be affected by their concentration in the product obtained from the dehydrohalogenation reaction. After the water is added to the reaction product, a portion of the compounds crystallize, forming an aqueous slurry, concurrent with formation of an organic phase. However, a substantial portion of the compounds remain in the organic phase using this method, and the addition of too much water may actually hinder crystallization. After the crystallization step, the organic phase is partially or totally stripped of phenolic hydroxyl group-containing or aromatic alkoxy group-containing (hereafter, collectively "phenolic-starting materials"), leaving the dihydroxy alkylstilbene compounds and some coproduct compounds of the reaction to prepare the dihydroxy alkylstilbene compounds formed during the preceding steps. It has been discovered that a portion of the dihydroxy alkylstilbene compounds present in the organic phase may be selectively crystallized utilizing the method described above. This method permits the recycle of the organic phase into the crystallization step of a separate batch of dehydrohalogenation reaction product, with the phenolic-starting materials present therein serving as a diluent. It has also been discovered that recycling the organic phase into the condensation reaction is not effective since it results in the degradation of the dihydroxy alkylstilbene compound, which further leads to the formation of an undesirable level of coproduct compounds. These and other advantages of the invention will be apparent from the description which follows.

DETAILED DESCRIPTION OF THE INVENTION

Figure 1:
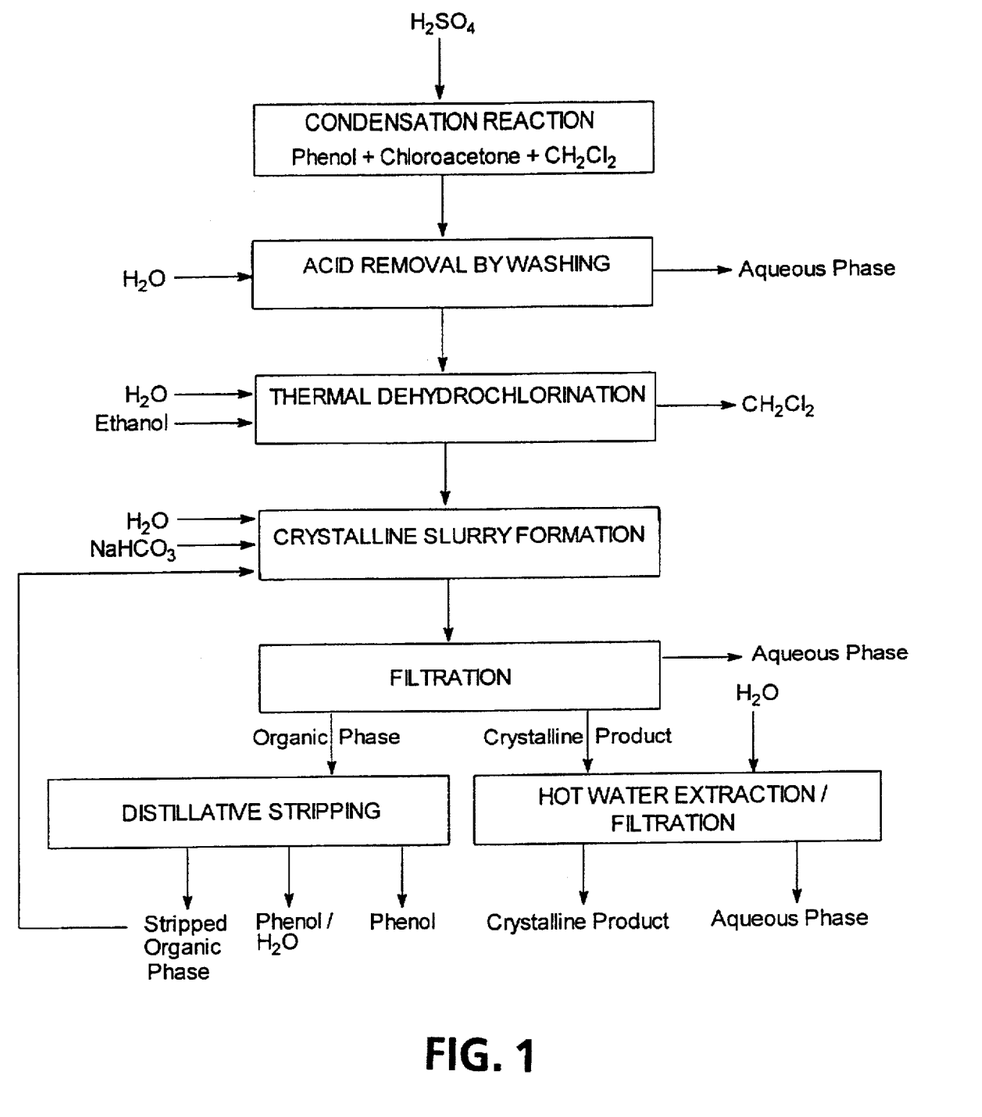
FIG. 1 is a process diagram of one embodiment of the invention.

The term "hydrocarbyl" as used herein means any aliphatic, cycloaliphatic, aromatic, aryl-substituted aliphatic, aryl substituted cycloaliphatic, aliphatic-substituted aromatic, or cycloaliphatic-substituted aromatic groups. The aliphatic or cycloaliphatic groups can be saturated or unsaturated. Likewise, the term "hydrocarbyloxy" means a hydrocarbyl group having an oxygen linkage between it and the carbon atom to which it is attached. The term "strong protonic acid" as employed herein means a proton donor (Brønsted acid) which on a thermodynamic acidity scale possesses a pKa value relative to water of $-0.5$ or less, preferably $-6$ or less. The term "Lewis acid" as used herein means a substance which is an electron-pair acceptor, that is, a substance with a vacant orbital. The term "water-immiscible solvent" as used herein, refers to a solvent that is not more than 10 percent, preferably not more than 5 percent, and most preferably not more than 3 percent soluble in water at 20° C.

Suitable phenolic hydroxyl-containing compounds which can be employed herein include most any monohydric phenol or phenolic compound represented by Formula I:

Formula I wherein each R is independently hydrogen or a hydrocarbyl or hydrocarbyloxy group having from 1 to 12, preferably 1 to 6, most preferably 1 to 4, carbon atoms, a halogen atom, preferably chlorine, bromine or fluorine, a nitro group, a nitrile group, or a —CO—R' group wherein R' is hydrogen or a hydrocarbyl group having from 1 to 8, preferably from 1 to 4, most preferably from 1 to 2, carbon atoms.

Particularly, suitable phenolic hydroxyl-containing compounds which can be employed herein to prepare the dihydroxy alkylstilbene(s) include, for example, phenol, 2,6-dimethylphenol, 2,6-diethylphenol, 2,6-dibromophenol, 2,6-dichlorophenol, 2,6-difluorophenol, 2,6-dimethoxyphenol, 2,6-diethylphenol, 3,5-dimethylphenol, 2-nitrophenol, 2-cyanophenol, 2-methylphenol, 3-methylphenol, 2-phenylphenol, 2-cyclohexylphenol, 2-octylphenol, 2-methyl-6-chlorophenol, 2-methoxy-6-chlorophenol, 2,3,5,6-tetramethylphenol, or any combination thereof. Phenol is most preferred as the phenolic hydroxyl-containing compound.

Suitable alkoxy group-containing aromatic compound(s) which can be employed herein include those compounds represented by Formula II:

Formula II wherein each R' is independently hydrogen or a hydrocarbyl group having from 1 to 12, preferably 1 to 6, most preferably 1 to 4, carbon atoms, a halogen atom, preferably chlorine, bromine or fluorine, a nitro group, a nitrile group, or a —CO—R' group wherein R' is hydrogen or a hydrocarbyl group having from 1 to 8, preferably from 1 to 4, most preferably from 1 to 2, carbon atoms; and $R^2$ is a hydrocarbyl group having from 1 to 12, preferably 1 to 2, most preferably 1, carbon atoms.

Particularly suitable alkoxy group-containing aromatic compound(s) which can be employed herein to prepare the dihydroxy alkylstilbenes include, for example, anisole, phenetole, 2,6-dimethylanisole, 2,6-diethylanisole, 2,6-dibromoanisole, 2,6-dichloroanisole, 2,6-difluoroanisole, 3,5-dimethylanisole, 2-nitroanisole, 2-cyanoanisole, 2-methylanisole, 3-methylanisole, 2-phenylanisole, 2-cyclohexylanisole, 2-octylanisole, 2-methyl-6-chloroanisole, 2-methoxy-6-chloroanisole, 2,3,5,6-tetramethylanisole, or any combination thereof. Anisole (methoxybenzene) is most preferred as the alkoxy group-containing aromatic compound.

Suitable alpha-haloketones which can be employed herein include; most any alpha-haloketone, such as, for example, those represented by Formula III:

Formula III wherein $R^3$ is hydrogen or a hydrocarbyl group having from 1 to 8, preferably 1 to 4, most preferably 1 to 2, carbon atoms; $R^4$ is a hydrocarbyl group having from 1 to 8, preferably 1 to 4, most preferably 1 carbon atoms; and X is a halogen atom, preferably chlorine or bromine.

When $R^3$ is other than hydrogen, the product produced will be a 4,4'-dihydroxy-alpha,alpha'-dialkylstilbene.

Particularly, suitable alpha-haloketones which can be employed herein to prepare the dihydroxy alkylstilbenes include, for example, chloroacetone, bromoacetone, 4-methyl-1-chloropentan-2-one, 1-chlorooctan-2-one, or any combination thereof. Chloroacetone is most preferred as the alpha-haloketone for preparing the dihydroxy alkylstilbenes.

Particularly, suitable alpha-haloketones which can be employed herein to prepare the 4,4'-dihydroxy-alpha,alpha'-dialkylstilbenes include, for example, 3-chlorobutan-2-one, 2-chloropentan-3-one, 3-chloro-pentan-2-one, 4-methyl-3-chloropentan-2-one, 4-methyl-2-chloropentan-3-one, or any combination thereof. 3-chlorobutan-2-one is most preferred as the alpha-haloketone for preparing the 4,4'-dihydroxy-alpha,alpha'-dialkylstilbenes.

The phenolic hydroxyl-containing compound(s) or alkoxy group-containing aromatic compound(s) and the alpha-haloketone(s) are employed in an amount such that the mole ratio of the phenolic-starting materials is from 0.1:1 to 20:1, preferably from 2.1:1 to 15:1, most preferably from 4:1 to 12:1. When the ratio of phenol:alpha-haloketone is greater than 20:1, excessive dilution of the reaction by phenolic hydroxyl-containing compound(s) or alkoxy group-containing aromatic compounds occurs. Additionally, more water-immiscible solvent may be required to keep the reaction mixture from freezing at the reaction temperatures used. When the ratio of phenol:alpha-haloketone is less than 0.1:1, excessive dilution of the reaction by alpha-haloketone occurs with an increase in the amount of unreacted alpha-haloketone which has to be removed at the end of the reaction.

Suitable strong protonic acids which can be employed herein include, for example, sulfuric acid, sulfuric acid containing sulfur trioxide, sulfonic acid form of a cation ion exchange resin such as, for example, polystyrene lightly crosslinked with divinylbenzene, methanesulfonic acid, ethanesulfonic acid, p-toluenesulfonic acid, hydrogen chloride, or any combination thereof. Concentrated sulfuric acid is most preferred as the strong protonic acid.

Suitable Lewis acids which can be employed herein include, for example, anhydrous aluminum chloride, tin tetrachloride, boron trifluoride, zinc chloride, boron trifluoride etherate, any combination thereof. Anhydrous aluminum chloride is most preferred as the Lewis acid. Combinations of strong protonic acids and Lewis acids can also be employed. These can be added sequentially, simultaneously or as preformed reaction products. $FSO_3H\text{-}SbF_5$ is an example of said preformed reaction products.

The strong protonic acid or Lewis acid is employed in an amount such that the mole ratio of phenolic hydroxyl-containing compound(s) or alkoxy group-containing aromatic compound(s):alpha-haloketone(s):strong protonic acid or Lewis acid is from 0.1:1:0.0026 to 20:1:8 preferably from 2.1:1:1 to 15:1:4, most preferably from 4:1:2 to 12:1:3.

In the process of the invention, step (A) may be carried out in the presence of a water-immiscible solvent. Suitable water-immiscible solvents include methylene chloride, chloroform, carbon tetrachloride, 1,2-dichloroethane, 1,1,1-trichloroethane, 1,1,2-trichloroethane, fluorotrichloromethane and bromotrichloromethane, or any combination thereof. Methylenechloride is most preferred as the water-immiscible solvent for preparing the dihydroxy alkylstilbenes.

The amount of the water-immiscible solvent used is dependent upon the nature of the reactants, and more critically dependent on the mode of the addition of the reactants. For example, when the alpha-haloketone is slowly added to the mixture containing the phenolic-starting material and the strong acid, less water-immiscible solvent is required to keep the reaction mixture from freezing at the reaction temperatures used than when the acid is added to a mixture containing the alpha-haloketone and the phenolic-starting material. The minimization of the water-immiscible solvent in the condensation reaction step (A) is desirable because the condensation reaction kinetics to form the desired intermediate are improved and the formation of undesirable trisphenolic coproducts are diminished.

In step (A) of the process of the present invention, the phenolic hydroxyl-containing compound(s) or alkoxy group-containing aromatic compound(s), the alpha-haloketone(s) and, optionally, the water-immiscible solvents, are combined together in the presence of a strong protonic or Lewis acid at a temperature in the range of from $-20°$ C. to $+20°$ C., preferably $-15°$ C. to $+10°$ C., most preferably $-13°$ C. to $0°$ C. Preferably, a protonic acid is employed, which is preferably combined first with the phenolic starting material and water-immiscible solvent, and then chilled to the desired reaction temperature prior to the addition of the alpha-haloketone. The alpha-haloketone is then added to the mixture of the phenolic-starting material and the strong protonic acid in the water-immiscible solvent at such a rate as to maintain the aforementioned temperatures for the reaction. The reaction can be conducted at any suitable pressure. The time required to complete the reaction depends upon the addition time of the alpha-haloketone, the reaction temperature, the heat transfer ability of the reactor employed and other such variables. Higher temperatures require shorter periods of time whereas lower temperatures require longer periods of time. Generally, however, times of from 5 minutes to 24 hours, preferably from 2 hours to 20 hours, most preferably from 4 hours to 18 hours are suitable. The reaction can be performed as a batch process or continuous process. It is frequently of benefit to conduct the reaction under an inert atmosphere, such as nitrogen, especially if the particular equipment used can entrain air which contains moisture.

It is typically desirable to choose a reaction time and temperature profile which provides the greatest conversion and selectivity to the halogen-containing bisphenol intermediate compound (hereafter, "intermediate compound") which, upon being dehydrohalogenated in step (C) of the process, forms the corresponding dihydroxy alkylstilbene. For the reaction employing phenol and chloroacetone as reactants in the presence of sulfuric acid, subjecting the reaction mixture to higher temperatures for prolonged periods of time, favors the formation of undesirable trisphenols, such as 1,2,2-tris(4-hydroxyphenyl)propane. Thus, it is frequently of value to conduct simple preliminary experiments over the range of reaction variables which can be employed in order to define an optimum reaction time and temperature profile which provides the greatest conversion and selectivity for the intermediate compound. In this manner, conditions not conducive to optimizing the yield of high purity dihydroxy alkylstilbene can be avoided.

Removal or neutralization of the strong protonic acid or Lewis acid and/or the products resulting from reaction of said acids during the reaction is accomplished in step (B) of the process of the invention using any unit operations which will effectively remove the acid such as washing with water, buffering, neutralization over a suitable ion exchange resin, neutralization with a basic-acting substance, such as, for example, alkali metal carbonates, bicarbonates or hydroxides such as, for example sodium bicarbonate, potassium bicarbonate, sodium hydroxide, or any combination thereof. When a Lewis acid such as anhydrous aluminum chloride is employed, initial neutralization with cold dilute hydrochloric acid is used as the initial step in the removal. It is also suitable to utilize combinations of unit operations which will effectively neutralize the acid in the reaction product, such as initially washing with water, followed by washing with an aqueous solution of a basic-acting substance. Likewise, the equipment associated with the aforementioned unit operations is chosen to maximize processability. Thus, for example, a centrifuge can be used to rapidly separate aqueous and organic layers resulting from the washing. A static coalescer can be used to induce rapid resolution of emulsified aqueous and organic layers resulting from the washing. In the case of the reaction crude prepared from phenol and chloroacetone, if the unit operations employed to remove the acid lead to an increase in temperature, especially above $10°$ C., then premature dehydrohalogenation of the intermediate compound to the dihydroxy alkylstilbene product may be observed.

When the acid content is reduced or eliminated by neutralization with a basic-acting substance, the basic-acting substance is usually employed in a stoichiometric or slightly less than the stoichiometric amount required to theoretically neutralize the desired proportion of the acid content.

The acid removal or neutralization step reduces the amount of strong protonic acids or Lewis acids or combination thereof and/or the products resulting from said acids in the reaction product to an amount less than 10,000 ppm, preferably less than 1,000 ppm, more preferably less than 250 ppm. This acid removal or neutralization step of the process can be conducted at temperatures of from −20° C. to 75° C., preferably from −5° C. to 50° C., more preferably from 0° C. to 10° C. At temperatures below −20° C., acid removal or neutralization can be hindered by freezing out of water if used for washing or as a solvent for the buffer or basic-acting substance. Temperatures below −20° C. also favor the formation and stabilization of emulsions, such as are formed in the washing process, thus making resolution of acid from the reaction product difficult.

At temperatures above 75° C., substantial dehydrohalogenation of the intermediate compound to the dihydroxy alkylstilbene product can induce premature precipitation of said product. Additionally, the higher temperatures can favor the formation of coproducts, such as trisphenol formed via reaction of intermediate compound with phenolic-starting material or via reaction of dihydroxy alkylstilbene with phenol, especially if the acid removal or neutralization process employed does not rapidly dilute the acid present in the reaction product.

In step (C) of the process of the invention, dehydrohalogenation of the intermediate compound to the dihydroxy alkylstilbene product is generally accomplished by heating of the washed reaction crude product from the acid removal step to a temperature of at least 20° C. to 150° C., preferably 50° C. to 90° C., most preferably 60° C. to 80° C. Once the desired temperature is achieved, it is maintained until completion of the dehydrohalogenation, typically from 1 second to 24 hours, preferably from 10 seconds to 6 hours, most preferably from 30 seconds to 3 hours. It is frequently desirable to monitor the course of the dehydrohalogenation via an analytical method, such as high pressure liquid chromatographic analysis. Additionally, it is frequently of value to conduct simple preliminary experiments over the range of reaction variables which can be employed in order to define an optimum reaction time and temperature profile which provides the greatest conversion and selectivity for the intermediate compound to the dihydroxy alkylstilbene product from the dehydrohalogenation step. In this manner, conditions not conducive to optimizing the yield of high purity dihydroxy alkylstilbene, can be avoided.

It is frequently of benefit to add water to the washed reaction crude prior to the dehydrohalogenation. This water serves to dilute any hydrogen halide released during the dehydrohalogenation and not volatilized out of the product and additionally dilutes any traces of acid incompletely removed from the reaction crude by the prior acid removal process, such as water washing. The amount of water varies depending upon the amount of water retained in the washed reaction crude, the amount of residual acid present in the washed reaction crude, the amount of acid expected to be liberated from the dehydrohalogenation, and other such variables. The water can also contain a neutralization agent, such as the aforementioned basic-acting substance, however, care must be taken that the amount of neutralization agent is not in an amount that causes the dehydrohalogenation reaction to be basic during the entire course of said reaction.

It is frequently of benefit to add one or more polar protic solvents in addition to the water added to the washed reaction crude just prior to the dehydrohalogenation. This polar protic solvent suitably serves to convert the biphasic dehydrohalogenation reaction to a monophasic dehydrohalogenation reaction. The amount of polar protic solvent required to form a monophasic mixture, that is, a uniform dispersion of the components so that the relative concentration of components of an aliquot from 1 part of the mixture is statistically indistinguishable from the concentration of components of an aliquot from any other part of the solution, is again application dependent, but is typically used in a volume-to-volume ratio of polar protic solvent to water of preferably not less than 1:1, more preferably not less than 2:1, and most preferably not less that 4:1; and preferably not more than 500:1, more preferably not more than 50:1, and most preferably not more than 20:1.

The concentration of the halogenated intermediate compound to be dehydrohalogenated is highly dependent on the nature of the polar protic solvent as well as the ratio of the polar protic solvent to water, but is preferably not more than 30 g, more preferably not more than 20 g, still more preferably not more than 15 g, and most preferably not more than 10 g per 100 mL of total solvent (that is, the polar protic solvent, the water and the water-immiscible solvent).

Suitable polar protic solvents include methanol, ethanol, n-propanol, isopropanol, n-butanol, isobutanol, ethylene glycol, ethylene glycol monomethyl ether, ethylene glycol monoethyl ether and diethylene glycol monomethyl ether. Most preferred as the polar protic solvents are ethanol and isopropanol.

During the dehydrohalogenation, stirring or mixing is desirable to assure even heating of the reaction crude and complete dispersion of the water, if added, and polar protic solvent, if added. During the course of the dehydrohalogenation, excess chloroacetone, if present, or water-immiscible solvent, if present, can be distilled from the mixture and recovered for further use. This distillation can be assisted by the application of a vacuum during the dehydrohalogenation step. The dehydrohalogenation process of the present invention may conveniently be ran using a batch process, as described hereinabove, or a continuous process, which may involve countercurrent flow of a stream of the washed condensation reaction product into a heated solution of polar protic solvent and water confined within a tubular reactor configuration. Alternately, a series of stirred tank reactors may be used in a continuous process.

In steps (D) and (G) of the process of the first aspect of the invention, and step (D) of the process of the second aspect of the invention, water is added to the dehydrohalogenation reaction product in amounts sufficient to crystallize at least a portion of the dihydroxy alkylstilbene. This serves to quench the dehydrohalogenation reaction by cooling and dilution of the reaction mixture, as well as to force precipitation of the crystalline dihydroxy alkylstilbene product. The amount of water used varies depending upon the structure of the particular dihydroxy alkylstilbene formed; the structure and amount of the reactants employed, especially the phenolic-starting material; the amount of water used in the dehydrohalogenation step; the amount of water retained in the washed reaction crude; and other such variables, but typically is used in an amount from 125 to 10, preferably from 100 to 30 most preferably from 40 to 80 percent by weight of the combined weight of the reaction crude and water used.

If desired, crystallization of the mixture of the dehydrohalogenation product and water can be induced or accelerated via the addition of seed crystals of the particular dihydroxy alkylstilbene product being prepared, however, this is typically unnecessary. It is frequently of value to conduct simple preliminary experiments over the range of time and temperature at which the crystalline slurry can be held in order to define an optimum time and temperature profile which provides the greatest isolated yield of the dihydroxy alkylstilbene product. Typically, the crystalline slurry is held at temperatures of from 0° C. to 60° C., preferably from 4° C. to 40° C., most preferably from 4° C. to 25° C. for a period of from 10 minutes to 1 week, preferably from 1 hour to 48 hours, most preferably from 8 hours to 24 hours. The product is recovered from the crystalline slurry using any unit operations which effectively remove the crystals from said slurry, such as, for example, filtration or centrifugation. The recovered product can be dried, for example, in an oven under vacuum, or utilized, as recovered as a wet cake. The liquid remaining after the removal of the crystals possesses an aqueous and an organic phase. The organic phase is recovered, for example, via decantation or separation in a separatory funnel.

When an alkoxy group-containing aromatic compound, such as anisole, is utilized in the process of the present invention, the resulting 4,4'-dialkoxy-alpha-alkylstilbene can be converted to the corresponding dihydroxy alkylstilbene using methods well established in the prior art. Such methods include, for example, (A) heating of the 4,4'-dialkoxy-alpha-alkylstilbene to reflux for 10 hours in 2,4,6-trimethylpyridine containing lithium iodide in the manner taught by I. T. Harrison, *Journal of Organic Chemistry*, Vol. 28, p. 2184 (1963); or (B) addition of the 4,4'-dialkoxy-alpha-alkylstilbene (may be as a solvent solution, for example, in methylene chloride, benzene, pentane, hexane) to boron tribromide (may be in solvent, for example, in methylene chloride, benzene, pentane, hexane) under a dry atmosphere, followed by reaction at 20° C. to 25° C. for 12 to 16 hours in the manner taught by J. F. W. McOmie, M. L. Watts and D. E. West, *Tetrahedron*, 24, 2289 (1968); or (C) refluxing of the 4,4'-dialkoxy-alpha-alkylstilbene in 48 percent hydrobromic acid in acetic acid for at least 30 minutes in the manner taught by I. Kawasaki, K. Matsuda and T. Kaneko, *Bulletin of the Chemical Society of Japan*, Vol. 44, 1986 (1971). All of the aforementioned citations are incorporated herein by reference in their entirety.

The organic phase recovered from step (D) is used in step (F) of the process of the first aspect of the invention by mixing the same with the dehydrohalogenation product obtained by independently repeating steps (A), (B), and (C). In the process of the second aspect of the invention, the organic phase recovered from step (D) is mixed with the slurry obtained by repeating steps (A), (B), (C), and (D). While the recovered organic phase may be used without further modification, its use is not preferred for reactions wherein an excess of phenolic-starting material with respect to alpha-haloketone was employed, as it can lead to the rapid buildup of said phenolic-starting material in amounts which may solubilize dihydroxy alkylstilbene product which would otherwise crystallize and thus be readily available for recovery. The organic phase is desirably stripped, for example, by vacuum distillation or falling film distillation, to remove at least about 20, more preferably at least about 50, most preferably at least about 80 percent by weight of the phenolic-starting material contained in said organic phase. While it is also operable to essentially completely strip phenolic-starting materials from the organic phase, this is not preferred as it produces a tacky, difficult to handle solid at room temperature, which requires prolonged mixing to disperse into the crystalline slurry formed in step (G) of the process of the second aspect of the invention. The phenolic hydroxyl group-containing compound recovered from stripping of the organic phase may be reused in the condensation reaction step (A)(2). Purification, such as, drying to remove water is typically required. It is frequently of value to add small amounts of a basic-acting substance such as, for example, sodium bicarbonate, to the organic phase prior to stripping, so as to neutralize any trace of acid either initially present or formed during the stripping.

When the organic phase is recovered after consecutive reactions and mixed back into the dehydrohalogenated product or the dehydrohalogenated product plus water, the desired balance between improved recovery of dihydroxy alkylstilbene and purity of dihydroxy alkylstilbene can be achieved via simple preliminary experiments over the range of reaction variables which can be employed in order to define the desired recovery and purity. If so desired, only part of the recovered organic phase may be recycled into the subsequent dehydrohalogenated product or the dehydrohalogenated product plus water so as to influence dihydroxy alkylstilbene recovery and purity obtained. Likewise, all or a part of the recovered organic phase may be subjected to one or more treatments prior to use in recycle so as to influence dihydroxy alkylstilbene recovery and purity obtained. An example of said treatments is thermal, catalytic or thermocatalytic dedimerization of the dimeric coproducts contained in said recovered organic phase as is taught by A. P. Haag et al. in "Process for the Preparation and Purification of 4,4'-Dihydroxy-alpha-substituted Stilbene," U.S. Ser. No. 08/608,807, filed Feb. 29, 1996, which is incorporated herein by reference.

The resultant dihydroxy alkylstilbene product can be further processed for the purpose of upgrading or otherwise modifying product purity by any of the techniques well known to the skilled artisan. Such techniques include, for example, extraction by water and/or organic solvents, recrystallization from organic solvents, sublimation, zone refining, crystal refining, column chromatography, or combinations thereof. A preferred method of post treatment is boiling water extraction of the dihydroxy alkylstilbene product recovered as a wet cake from the dehydrohalogenation step. In this method, the dihydroxy alkylstilbene product is slurried in water, brought to a boil and either filtered hot, or cooled and then filtered.

When a phenolic hydroxyl-containing compound is employed the resultant dihydroxy alkylstilbene compound is believed to be a compound represented by Formula IV:

Formula IV wherein each R, $R^3$ and $R^4$ are as previously defined.

When an alkoxy group-containing aromatic compound is employed and the resultant 4,4'-dialkoxy-alpha-alkylstilbene is dealkylated, the resultant dihydroxy alkylstilbene compound is believed to be a compound represented by Formula V:

Formula V wherein each R', R³ and R⁴ are as previously defined.

The product actually produced is a mixture of cis-and trans-isomers with the trans-isomer being predominant.

The high purity dihydroxy alkylstilbene products obtainable by the process of the present invention are useful for the advancement of epoxy resins, for the preparation of phenoxy or epoxy resins, and for the preparation of liquid-crystalline thermoplastics such as polyarylates.

The following examples are for illustrative purposes only and are not intended to limit the scope of this invention.

EXAMPLE 1

Synthesis Of 4,4'-Dihydroxy-α-methylstilbene Employing Recycle of Stripped Organic Phase into the Crystalline Slurry Formation Step A series of 5 synthetic reactions are carried out as described below, with recycle of stripped organic phase from the preceding reaction into the next reaction in sequence. Thus, recycle commences with the stripped organic phase from the initial reaction being recycled into the second reaction, the stripped organic phase from the second reaction being recycled into the third reaction, and so on. To recycle the stripped organic phase, it is added to the crystalline slurry formed after completion of the dehydrochlorination reaction. The organic phase is prepared for recycle by rotary evaporation to remove the phenol/water azeotrope and part of the phenol from the organic phase separated out from the filtrate recovered from the filtration of the crystalline slurry which forms after dehydrochlorination. Visual appearance of the organic phase is used to determine the endpoint for the rotary evaporations. Thus, when the first crystalline precipitate appears in the organic phase during the stripping of phenolic-starting material at 85° C. to 89° C. and 1 mm Hg of vacuum, the rotary evaporation is terminated and the resultant stripped organic phase deemed ready for use in recycle. All 5 reactions are completed using a 15:1:1 mole ratio of phenol:chloroacetone:sulfuric acid, respectively, in the condensation step with essentially identical reaction conditions throughout the series (a time/temperature profile which gives partial chloroacetone conversion, typically 85 percent). The chloroacetone employed is a commercial grade containing 96.5 percent chloroacetone, 3.0 percent 1,1-dichloroacetone, 0.40 percent mesityl oxide, 0.05 percent acetone and 0.05 percent higher boiling compounds. The term "dimer I" as used hereafter means trans-1,2,4,5-tetrakis(4-hydroxyphenyl)-4-methylpentene and the term "dimer II" refers to the corresponding cis-isomer. Specific details for each of the 5 reactions are delineated in the following sections:

A. Initial Synthesis of 4,4'-Dihydroxy-alpha-methylstilbene

Phenol (1411.5 g, 15.0 moles), chloroacetone (95.5 g, 1.0 mole as chloroacetone) and methylene chloride (2650 g) are added to a 5-liter glass reactor equipped with a chilled ethylene glycol-water condenser (−5° C.), mechanical stirrer, nitrogen purge (1 liter per minute), thermometer, dropping funnel and jacket for circulating coolant over the reactor exterior. Stirring commences concurrent with cooling of the reactant solution to −10° C. Sulfuric acid (98.1 g, 1.0 mole) is added to the dropping funnel, then dropwise addition to the stirred reactant solution commenced over a 64-minute period and so as to maintain the reaction temperature between −10° C. and −14° C. After 15 hours 5 minutes of post reaction at −13° C. to −14° C., chilled (4° C.) deionized water (1950 g) is added to the stirred reaction product inducing a maximum increase in temperature to −1° C. After 1 minute of mixing, the opaque, pale-pink colored product is recovered (5857.2 g) and equally divided into three 2-liter glass separatory funnels. After settling, the resolved aqueous layer comprising 1490.3 g is separated off. The recovered organic layer comprising 4369.0 g is equally divided into the three 2-liter glass separatory funnels, then the contents of each of the 3 separatory funnels are sequentially washed 4 times each with 500-g portions of chilled deionized water, with the following amounts recovered:

Wash 1: Organic Layer=4517.3 g. Aqueous Layer=1328.4 g.
Wash 2: Organic Layer=4800.8 g. Aqueous Layer=1175.4 g.
Wash 3: Organic Layer=4792.8 g. Aqueous Layer=1481.8 g.
Wash 4: Organic Layer=3894.9 g. Aqueous Layer=2370.4 g.

The organic layers are recovered and combined, and a portion (approximately 0.1 g) of the washed organic is removed and analyzed by HPLC analysis using a uv detector set at 254 nm. This analysis provides the distribution of components in their relative order of elution summarized in Table I, as follows:

TABLE I

CONDENSATION REACTION PRODUCT: INITIAL SYNTHESIS

| Compound | Area percent |
|---|---|
| phenolsulfonic acids | 0.21 |
| chloroacetone | trace |
| phenol | 93.90 |
| 1,2,2-tris(4-hydroxyphenyl)propane | trace |
| 4,4'-dihydroxy-α-methylstilbene | 0.28 |
| 1,2-bis(4-hydroxyphenyl)-2-chloropropane | 5.13 |
| oligomer | 0.48 |

The combined organic layers are equally split into three 4-liter glass beakers equipped with magnetic stirring, along with deionized water (250 g per beaker). The biphasic mixtures in the beakers are stirred during heating to 80° C. Methylene chloride is vented from the stirred beakers during heating. Once the 80° C. temperature is achieved, heating ceases and the dehydrochlorinated reaction mixture in each beaker is quenched by the addition of deionized water (1000 mL). Quenching decreases the temperature to 48° C. An excess of sodium bicarbonate (30 g) is added to each beaker to provide a neutral pH. After the sodium bicarbonate addition, the beakers are covered and allowed to stir overnight under ambient conditions. The crystalline slurries resulting from the quenched dehydrochlorination reaction are filtered via vacuum filtration through a coarse-fritted glass funnel. The cake on the filter is packed and maintained on the filter until no more filtrate is observed to come off. The filtrate from the crystalline slurries is added to a separatory funnel and split to provide 1229.04 g of organic phase, with the aqueous phase discarded. The wet cake is recovered from the filter and added to a 1-liter glass beaker along with deionized water (250 g) then heated to 100° C. concurrent with magnetic stirring. After 1 minute at 100° C., the stirred slurry is filtered while hot through a coarse-fritted glass filter. The crystalline product cake is packed then washed on the filter with boiling deionized water (100 g). The product recovered from the filter is dried in a vacuum oven at 80° C. and 1 mm Hg to a constant weight of 40.9 g of white crystalline product. HPLC analysis using a uv detector set at 220 nm of a portion of the crystalline product provides the following distribution of components in their relative order of elution (Table II). The data is unnormalized with respect to unknowns and impurities in the HPLC solvents and on the HPLC column.

TABLE II

FINAL CRYSTALLINE PRODUCT: INITIAL SYNTHESIS

| Compound | Area percent |
| --- | --- |
| phenol | 0.34 |
| 1,2,2-tris(4-hydroxyphenyl)propane | 0.15 |
| trans-4,4'-dihydroxy-α-methylstilbene | 91.33 |
| 2,3-bis(4-hydroxyphenyl)propene | 2.41 |
| dimer I | 1.68 |
| cis-4,4'-dihydroxy-α-methylstilbene | 1.67 |
| dimer II | 0.08 |

B. Second Sequential Synthesis of 4,4'-Dihydroxy-α-methylstilbene with Recycle from the Initial Synthesis The organic phase (1229.04 g) from the initial synthesis of 4,4'-dihydroxy-α-methylstilbene is added to a 2-liter glass RB flask and stripped on a rotary evaporator concurrent with the workup (washing, dehydrochlorination) of the condensation reaction product from the present reaction. A total time of 115 minutes at a temperature range of 71° C. to 85° C. and a 1 mm Hg vacuum are used for the rotary evaporation. At this time, the first crystals (presumably of trans-4,4'-dihydroxy-α-methylstilbene) are observed to form in the 85° C. organic product and this is used as an indicator to cease rotary evaporation. During the rotary evaporation, 802.4 g of distillate is recovered and analyzed for water and chloroacetone by externally standardized gas chromatographic analysis using a thermal conductivity detector. Phenol is calculated by difference. This analysis reveals the presence of 18.88 weight percent water, 1.85 weight percent chloroacetone and 78.27 weight percent phenol. The total weight of organic mixture recovered for recycle is 213.9 g (17.4 percent of the organic phase weight remaining after stripping). HPLC analysis using a uv detector set at 254 nm of a portion of the organic reveals the presence of 31.4 area percent phenol and 44.1 area percent 4,4'-dihydroxy-α-methylstilbene, plus multiple unidentified higher retention time peaks. The balance (212.74 g by difference) is observed as liquid in the cold traps between the, rotary evaporator and the vacuum pump. The amount of phenol recovered in the distillate represents 44.5 weight percent of the initial phenol used in the condensation reaction. The amount of unreacted chloroacetone recovered in the distillate demonstrates 83.96 percent conversion of the chloroacetone reactant to products in the initial reaction.

Phenol (1411.5 g, 15.0 moles), chloroacetone (95.5 g, 1.0 mole as chloroacetone) and methylene chloride (2650 g) are added to a 5-liter glass reactor equipped with a chilled ethylene glycol-water condenser (−5° C.), mechanical stirrer, nitrogen purge (1 liter per minute), thermometer, dropping funnel and jacket for circulating coolant over the reactor exterior. Stirring commences concurrent with cooling of the reactant solution to −10° C. Sulfuric acid (98.1 g, 1.0 mole) is added to the dropping funnel, then dropwise addition of sulfuric acid to the stirred reactant solution commences over a 64-minute period at a rate which maintains the reaction temperature between −10° C. and −14° C. After 16 hours 18 minutes of post reaction at −14° C., a portion (approximately 0.1 g) of the condensation reaction product is removed and analyzed by HPLC using a uv detector set at 254 nm. This analysis provides the following distribution of components in their relative order of elution summarized in Table III:

TABLE III

CONDENSATION REACTION PRODUCT: SECOND SYNTHESIS

| Compound | Area percent |
| --- | --- |
| phenolsulfonic acids | 0.25 |
| chloroacetone | trace |
| phenol | 93.58 |
| 1,2,2-tris(4-hydroxyphenyl)propane | trace |
| 4,4'-dihydroxy-α-methylstilbene | 0.56 |
| 1,2-bis(4-hydroxyphenyl)-2-chloropropane | 4.99 |
| oligomer | 0.62 |

At this time, chilled (4° C.) deionized water (1950 g) is added to the stirred reaction product inducing a maximum increase in temperature to −1° C. After 1 minute of mixing, the opaque, pale-pink colored product is recovered (5827.8 g) and equally divided into three 2-liter glass separatory funnels. After settling, the resolved aqueous layer comprising 1471.7 g is separated off. The recovered organic layer comprising 4335.1 g is equally divided into the three 2-liter glass separatory funnels, then the contents of each of the 3 separatory funnels are sequentially washed 4 times each with 500-g portions of chilled deionized water, with the following amounts recovered:

Wash 1: Organic Layer=4316.1 g. Aqueous Layer=1496.6 g.

Wash 2: Organic Layer=4240.3 g. Aqueous Layer=1547.9 g.

Wash 3: Organic Layer=3767.5 g. Aqueous Layer=1947.8 g.

Wash 4: Organic Layer=3543.8 g. Aqueous Layer=1699.4 g.

The combined organic layers are equally split into three 4-liter glass beakers equipped with magnetic stirring, along with deionized water (250 g per beaker). The biphasic mixtures in the beakers are stirred during heating to 80° C. Methylene chloride is vented from the stirred beakers during heating. Once the 80° C. temperature is achieved, heating ceases and the dehydrochlorinated reaction mixture in each beaker is quenched by the addition of deionized water (1000 mL). Quenching decreases the temperature to 48° C. An excess of sodium bicarbonate (30 g) is added to each beaker to provide a neutral pH. Immediately after the sodium bicarbonate addition, 69.1 g of the stripped organic phase for recycle is added to each of the beakers for a total of 207.5 g. Thus, 6.4 g of the original 213.9 g of stripped organic phase for recycle is not added because it crystallized on the walls of the glass flask in which it is contained and could not be readily removed. After the stripped organic phase addition, the beakers are covered and allowed to stir overnight under ambient conditions. The crystalline slurries resulting from the quenched dehydrochlorination reaction are filtered via vacuum filtration through a coarse-fritted glass funnel. The cake on the filter is packed and maintained on the filter until no more filtrate is observed to come off. The filtrate from the crystalline slurry is added to a separatory funnel and split to provide 1424.7 g of organic phase, with the aqueous phase discarded. The wet cake is recovered from the filter and added to a 1-liter glass beaker along with deionized water (250 g) then heated to 100° C. concurrent with magnetic stirring. After 1 minute at 100° C., the stirred slurry is filtered while hot through a coarse-fritted glass filter. The crystalline product cake is packed, then washed on the filter with boiling deionized water (100 g). The product recovered from the filter is dried in a vacuum oven at 80° C. and 1 mm Hg to a constant weight of 67.6 g of white crystalline product. HPLC analysis using a uv detector set at 220 nm of a portion of the crystalline product provides the following distribution of components in their relative order of elution (Table IV). The data is unnormalized with respect to unknowns and impurities in the HPLC solvents and on the HPLC column.

TABLE IV

FINAL CRYSTALLINE PRODUCT: SECOND SYNTHESIS

| Compound | Area percent |
| --- | --- |
| phenol | 0.39 |
| 1,2,2-tris(4-hydroxyphenyl)propane | trace |
| trans-4,4'-dihydroxy-α-methylstilbene | 91.59 |
| 2,3-bis(4-hydroxyphenyl)propene | 0.32 |
| dimer I | 2.14 |
| cis-4,4'-dihydroxy-α-methylstilbene | 3.80 |
| dimer II | 0.13 |

C. Third Sequential Synthesis of 4,4'-Dihydroxy-α-methylstilbene with Recycle from the Second Synthesis The organic phase (1424.7 g) from the second synthesis of 4,4'-dihydroxy-α-methylstilbene is added to a 2-liter glass RB flask and stripped on a rotary evaporator concurrent with the workup (washing, dehydrochlorination) of the condensation reaction product from the present reaction. A total time of 130 minutes at a temperature range of 74° C. to 89° C. and a 1 mm Hg vacuum are used for the rotary evaporation. At this time, the first crystals (presumably of trans-4,4'-dihydroxy-α-methylstilbene) are observed to form in the 89° C. organic product and this is used as an indicator to cease rotary evaporation. During the rotary evaporation, 927.5 g of distillate is recovered and analyzed for water and chloroacetone by externally standardized gas chromatographic analysis using a thermal conductivity detector. Phenol is calculated by difference. This analysis reveals the presence of 18.93 weight percent water, 1.24 weight percent chloroacetone and 79.83 weight percent phenol. The total weight of organic mixture recovered for recycle is 217.3 g (15.3 percent of the organic phase weight remaining after stripping). HPLC analysis using a uv detector set at 254 nm of a portion of the organic mixture reveals the presence of 18.3 area percent phenol and 42.2 area percent 4,4'-dihydroxy-α-methylstilbene, plus multiple unidentified higher retention time peaks. The balance (279.9 g by difference) is observed as liquid in the cold traps between the rotary evaporator and the vacuum pump. The amount of phenol recovered in the distillate represents 52.5 weight percent of the initial phenol used in the condensation reaction. The amount of unreacted chloroacetone recovered in the distillate demonstrates 87.58 percent conversion of the chloroacetone reactant to products in the second reaction.

Phenol (1411.5 g, 15.0 moles), chloroacetone (95.5 g, 1.0 mole as chloroacetone) and methylene chloride (2650 g) are added to a 5-liter glass reactor equipped with a chilled ethylene glycol-water condenser (−5° C.), mechanical stirrer, nitrogen purge (1 liter per minute), thermometer, dropping funnel and jacket for circulating coolant over the reactor exterior. Stirring commences concurrent with cooling of the reactant solution to −10° C. Sulfuric acid (98.1 g, 1.0 mole) is added to the dropping funnel, then dropwise addition to the stirred reactant solution commences over a 45-minute period and so as to maintain the reaction temperature between −10° C. and −13° C. After 20 hours 55 minutes of post reaction at −13° C., a portion (approximately 0.1 g) of the condensation reaction product is removed and analyzed by HPLC using a uv detector set at 254 nm. This analysis provides the following distribution of components in their relative order of elution summarized in Table V:

TABLE V

CONDENSATION REACTION PRODUCT: THIRD SYNTHESIS

| Compound | Area percent |
| --- | --- |
| phenolsulfonic acids | 0.37 |
| chloroacetone | trace |
| phenol | 92.63 |
| 1,2,2-tris(4-hydroxyphenyl)propane | 0.24 |
| 4,4'-dihydroxy-α-methylstilbene | 0.60 |
| 1,2-bis(4-hydroxyphenyl)-2-chloropropane | 5.51 |
| oligomer | 0.65 |

At this time, chilled (4° C.) deionized water (1950 g) is added to the stirred reaction product inducing a maximum increase in temperature to −1° C. After 1 minute of mixing, the opaque, pale-pink colored product is recovered (5855.6 g) and equally divided into three 2-liter glass separatory funnels. After settling, the resolved aqueous layer comprising 1302.1 g is separated off. The recovered organic layer comprising 4533.4 g is equally divided into the three 2-liter glass separatory funnels, then the contents of each of the 3 separatory funnels are sequentially washed 4 times each with 500-g portions of chilled deionized water, with the following amounts recovered:

Wash 1: Organic Layer=4764.0 g. Aqueous Layer=1237.5 g.

Wash 2: Organic Layer=4635.1 g. Aqueous Layer=1605.0 g.

Wash 3: Organic Layer=4461.1 g. Aqueous Layer=1642.5 g.

Wash 4: Organic Layer=3699.0 g. Aqueous Layer=2235.9 g.

The combined organic layers are equally split into three 4-liter glass beakers equipped with magnetic stirring, along with deionized water (250 g per beaker). The biphasic mixtures in the beakers are stirred during heating to 80° C. Methylene chloride is vented from the stirred beakers during heating. Once the 80° C. temperature is achieved, heating ceases and the dehydrochlorinated reaction mixture in each beaker is quenched by the addition of deionized water (1000 ml). Quenching decreases the temperature to 48° C. An excess of sodium bicarbonate (30 g) is added to each beaker to provide a neutral pH. Immediately after the sodium bicarbonate addition, 66.36 g of the stripped organic phase for recycle is added to each of the beakers for a total of 199.09 g. Thus, 18.21 g of the original 217.3 g of stripped organic phase for recycle is not added because it crystallized on the walls of the glass flask in which it is contained and could not be readily removed. After the stripped organic phase addition, the beakers are covered and allowed to stir overnight under ambient conditions. The crystalline slurries resulting from the quenched dehydrochlorination reaction are filtered via vacuum filtration through a coarse-fritted glass funnel. The cake on the filter is packed and maintained on the filter until no more filtrate is observed to come off. The filtrate from the crystalline slurry is added to a separatory funnel and split to provide 1391.0 g of organic phase, with the aqueous phase discarded. The wet cake is recovered from the filter and added to a 1-liter glass beaker along with deionized water (250 g) then heated to 100° C. concurrent with magnetic stirring. After 1 minute at 100° C., the stirred slurry is filtered while hot through a coarse-fritted glass filter. The crystalline product cake is packed then washed on the filter with boiling deionized water (100 g). The product recovered from the filter is dried in a vacuum oven at 80° C. and 1 mm Hg to a constant weight of 94.4 g of white crystalline product. HPLC analysis using a uv detector set at 220 nm of a portion of the crystalline product provides the following distribution of components in their relative order of elution (Table VI). The data is unnormalized with respect to unknowns and impurities in the HPLC solvents and on the HPLC column.

TABLE VI

FINAL CRYSTALLINE PRODUCT: THIRD SYNTHESIS

| Compound | Area percent |
| --- | --- |
| phenol | 0.43 |
| 1,2,2-tris(4-hydroxyphenyl)propane | 0.17 |
| trans-4,4'-dihydroxy-α-methylstilbene | 90.29 |
| 2,3-bis(4-hydroxyphenyl)propene | 0.68 |
| dimer I | 2.67 |
| cis-4,4'-dihydroxy-α-methylstilbene | 2.52 |
| dimer II | 0.29 |

D. Fourth Sequential Synthesis of 4,4'-Dihydroxy-α-methylstilbene with Recycle from the Third Synthesis The organic phase (1391.0 grams) from the third synthesis of 4,4'-dihydroxy-α-methylstilbene (Run 062794) is added to a 2-liter glass RB flask and stripped on a rotary evaporator concurrent with the workup (washing, dehydrochlorination) of the condensation reaction product from the present reaction. A total time of 137 minutes at a temperature range of 75° C. to 86° C. and a 1 mm Hg vacuum are used for the rotary evaporation. At this time, the first crystals (presumably of trans-4,4'-dihydroxy-α-methylstilbene) are observed to form in the 86° C. organic product and this is used as an indicator to cease rotary evaporation. During the rotary evaporation, 882.1 g of distillate is recovered and analyzed for water and chloroacetone by externally standardized gas chromatographic analysis using a thermal conductivity detector. Phenol is calculated by difference. This analysis reveals the presence of 11.18 weight percent water, 1.47 weight percent chloroacetone and 87.35 weight percent phenol. The total weight of organic mixture recovered for recycle is 247.8 g (17.8 percent of the organic phase weight remaining after stripping). The balance (350.2 g by difference) is observed as liquid in the cold traps between the rotary evaporator and the vacuum pump. The amount of phenol recovered in the distillate represents 54.6 weight percent of the initial phenol used in the condensation reaction. The amount of unreacted chloroacetone recovered in the distillate demonstrates 85.99 percent conversion of the chloroacetone reactant to products in the third reaction.

Phenol (1411.5 g, 15.0 moles), chloroacetone (95.5 g, 1.0 mole as chloroacetone) and methylene chloride (2650 g) are added to a 5-liter glass reactor equipped with a chilled ethylene glycol-water condenser (−5° C.), mechanical stirrer, nitrogen purge (1 liter per minute), thermometer, dropping funnel and jacket for circulating coolant over the reactor exterior. Stirring commenced concurrent with cooling of the reactant solution to −10° C. Sulfuric acid (98.1 g, 1.0 mole) is added to the dropping funnel, then dropwise addition to the stirred reactant solution commences over a 51-minute period and so as to maintain the reaction temperature between −10° and −13° C. After 15 hours 58 minutes of post reaction at −13° C. to −14° C., a portion (approximately 0.1 g) of the condensation reaction product is removed and analyzed by HPLC using a uv detector set at 220 nm. This analysis provides the following distribution of components in their relative order of elution summarized in Table VII:

TABLE VII

CONDENSATION REACTION PRODUCT: FOURTH SYNTHESIS

| Compound | Area percent |
| --- | --- |
| phenolsulfonic acids | trace |
| chloroacetone | trace |
| phenol | 92.63 |
| 1,2,2-tris(4-hydroxyphenyl)propane | trace |
| 4,4'-dihydroxy-α-methylstilbene | trace |
| 1,2-bis(4-hydroxyphenyl)-2-chloropropane | 5.29 |
| oligomer | trace |

At this time, chilled (4° C.) deionized water (1950 g) is added to the stirred reaction product inducing a maximum increase in temperature to −1° C. After 1 minute of mixing, the opaque, pale-pink colored product is recovered (5825.9 g) and equally divided into three 2-liter glass separatory funnels. After settling, the resolved aqueous layer comprising 1307.2 g is separated off. The recovered organic layer comprising 4493.9 g is equally divided into the three 2-liter glass separatory funnels, then the contents of each of the 3 separatory funnels are sequentially washed 4 times each with 500-g portions of chilled deionized water, with the following amounts recovered:

Wash 1: Organic Layer=4846.6 g. Aqueous Layer=1122.2 g.

Wash 2: Organic Layer=4423.5 g. Aqueous Layer=1894.9 g.

Wash 3: Organic Layer=3868.1 g. Aqueous Layer=2026.5 g.

Wash 4: Organic Layer=3601.2 g. Aqueous Layer=1737.2 g.

The combined organic layers are equally split into three 4-liter glass beakers equipped with magnetic stirring, along with deionized water (250 g per beaker). The biphasic mixtures in the beakers are stirred during heating to 80° C. Methylene chloride is vented from the stirred beakers during heating. Once the 80° C. temperature is achieved, heating ceases and the dehydrochlorinated reaction mixture in each beaker is quenched by the addition of deionized water (1000 mL). Quenching decreases the temperature to 48° C. An excess of sodium bicarbonate (30 g) is added to each beaker to provide a neutral pH. Immediately after the sodium bicarbonate addition, 82.6 g of the stripped organic phase for recycle is added to each of the beakers for a total of 247.8 g. (The stripped organic phase for recycle which crystallized on the walls of the glass flask in which it is contained is washed out with a small amount of methylene chloride. This methylene chloride solution is placed in a clean 4-liter glass beaker and the solvent evaporated off. The contents of the beaker requiring this stripped organic phase to contain the full 82.6 g are then emptied into the 4-liter beaker into which the solvent-borne transfer had been made. In this manner, the entire 247.8 g of stripped organic phase is recycled). After the stripped organic phase addition, the beakers are covered and allowed to stir overnight under ambient conditions. The crystalline slurries resulting from the quenched dehydrochlorination reaction are filtered via vacuum filtration through a coarse fritted glass funnel. The cake on the filter is packed and maintained on the filter until no more filtrate is observed to come off. The filtrate from the crystalline slurry is added to a separatory funnel and split to provide 1480.1 g of organic phase, with the aqueous phase discarded. The wet cake is recovered from the filter and added to a 1-liter glass beaker along with deionized water (250 g) then heated to 100° C. concurrent with magnetic stirring. After 1 minute at 100° C., the stirred slurry is filtered while hot through a coarse-fritted glass filter. The crystalline product cake is packed, then washed on the filter with boiling deionized water (100 g). The product recovered from the filter is dried in a vacuum oven at 80° C. and 1 mm Hg to a constant weight of 82.64 g of white crystalline product. HPLC analysis using a uv detector set at 220 nm of a portion of the crystalline product provides the following distribution of components in their relative order of elution (Table VIII). The data is unnormalized with respect to unknowns and impurities in the HPLC solvents and on the HPLC column.

TABLE VIII

FINAL CRYSTALLINE PRODUCT: FOURTH SYNTHESIS

| Compound | Area percent |
|---|---|
| phenol | 0.38 |
| 1,2,2-tris(4-hydroxyphenyl)propane | 0.67 |
| trans-4,4'-dihydroxy-α-methylstilbene | 91.17 |
| 2,3-bis(4-hydroxyphenyl)propene | 0.30 |
| dimer I | 2.69 |
| cis-4,4'-dihydroxy-α-methylstilbene | 1.39 |
| dihydroxy-α-methylstilbene isomer | 0.18 |
| dimer II | 0.47 |

E. Fifth Sequential Synthesis of 4,4'-Dihydroxy-α-methylstilbene with Recycle from the Fourth Synthesis The organic phase (1480.1 g) from the fourth synthesis of 4,4'-dihydroxy-α-methylstilbene (Run 070595) is added to a 2-liter glass RB flask and stripped on a rotary evaporator concurrent with the workup (washing, dehydrochlorination) of the condensation reaction product from the present reaction. A total time of 150 minutes at a temperature range of 74° C. to 87° C. and a 1 mm Hg vacuum are used for the rotary evaporation. At this time, the first crystals (presumably of trans-4,4'-dihydroxy-α-methylstilbene) are observed to form in the 87° C. organic product and this is used as an indicator to cease rotary evaporation. During the rotary evaporation, 940.8 g of distillate is recovered and analyzed for water and chloroacetone by externally standardized gas chromatographic analysis using a thermal conductivity detector. Phenol is calculated by difference. This analysis reveals the presence of 12.91 weight percent water, 1.77 weight percent chloroacetone and 85.32 weight percent phenol. The total weight of organic mixture recovered for recycle is 276.6 g (18.7 percent of the organic phase weight remaining after stripping). HPLC analysis using a uv detector set at 254 nm of a portion of the organic mixture reveals the presence of 12.7 area percent phenol and 38.1 area percent 4,4-dihydroxy-α-methylstilbene, plus multiple unidentified higher retention time peaks. The balance (262.7 g by difference) is observed as liquid in the cold traps between the rotary evaporator and the vacuum pump. The amount of phenol recovered in the distillate represents 56.9 weight percent of the initial phenol used in the condensation reaction. The amount of unreacted chloroacetone recovered in the distillate demonstrates 82.01 percent conversion of the chloroacetone reactant to products in the fourth reaction.

Phenol (1411.5 g, 15.0 moles), chloroacetone (95.5 g, 1.0 mole as chloroacetone) and methylenl chloride (2650 g) are added to a 5-liter glass reactor equipped with a chilled ethylene glycol-water condenser (−5° C.), mechanical stirrer, nitrogen purge (1 liter per minute), thermometer, dropping funnel and jacket for circulating coolant over the reactor exterior. Stirring commenced concurrent with cooling of the reactant solution to −10° C. Sulfuric acid (98.1 g, 1.0 mole) is added to the dropping funnel, then dropwise addition to the stirred reactant solution commenced over a 34-minute period and so as to maintain the reaction temperature between −10° C. and −13° C. After 16 hours 33 minutes of post reaction at −13° C. to −14° C., a portion (approximately 0.1 g) of the condensation reaction product is removed and analyzed by HPLC using a uv detector set at 254 nm. This analysis provides the following distribution of components in their relative order of elution summarized in Table IX:

TABLE IX

CONDENSATION REACTION PRODUCT: FIFTH SYNTHESIS

| Compound | Area percent |
|---|---|
| phenolsulfonic acids | 0.16 |
| chloroacetone | trace |
| phenol | 94.81 |
| 1,2,2-tris(4-hydroxyphenyl)propane | trace |
| 4,4'-dihydroxy-α-methylstilbene | trace |
| 1,2-bis(4-hydroxyphenyl)-2-chloropropane | 4.45 |
| oligomer | 0.58 |

At this time, chilled (4° C.) deionized water (1950 g) is added to the stirred reaction product inducing a maximum increase in temperature to −1° C. After 1 minute of mixing, the opaque, pale-pink colored product is recovered (5822.3 g) and equally divided into three 2-liter glass separatory funnels. After settling, the resolved aqueous layer comprising 1325.3 g is separated off. The recovered organic layer comprising 4475.6 g is equally divided into the three 2-liter glass separatory funnels, then the contents of each of the 3 separatory funnels are sequentially washed 4 times each with 500-g portions of chilled deionized water, with the following amounts recovered:

Wash 1: Organic Layer=4343.9 g. Aqueous Layer=1599.2 g.

Wash 2: Organic Layer=4160.3 g. Aqueous Layer=1650.8 g.

Wash 3: Organic Layer=3937.7 g. Aqueous Layer=1693.4 g.

Wash 4: Organic Layer=3604.9 g. Aqueous Layer=1705.4 g.

The combined organic layers are equally split into three 4-liter glass beakers equipped with magnetic stirring, along with deionized water (250 g per beaker). The biphasic mixtures in the beakers are stirred during heating to 80° C. Methylene chloride is vented from the stirred beakers during heating. Once the 80° C. temperature is achieved, heating ceases and the dehydrochlorinated reaction mixture in each beaker is quenched by the addition of deionized water (1000 mL). Quenching decreases the temperature to 48° C. An excess of sodium bicarbonate (30 g) is added to each beaker to provide a neutral pH. Immediately after the sodium bicarbonate addition, 92.2 g of the stripped organic mixture for recycle is added to each of the beakers for a total of 276.6 g. (The stripped organic phase for recycle which crystallized on the walls of the glass flask in which it is contained is washed out with a small amount of methylene chloride. This methylene chloride solution is placed in a clean 4-liter glass beaker and the solvent evaporated off. The contents of the beaker requiring this stripped organic phase to contain the full 92.2 g are then emptied into the 4-liter beaker into which the solvent borne transfer had been made. In this manner, the entire 276.6 g of stripped organic phase is recycled). After the stripped organic phase addition, the beakers are covered and allowed to stir overnight under ambient conditions. The crystalline slurries resulting from the quenched dehydrochlorination reaction are filtered via vacuum filtration through a coarse-fritted glass funnel. The cake on the filter is packed and maintained on the filter until no more filtrate is observed to come off. The filtrate from the crystalline slurry is added to a separatory funnel and split to provide 1517.3 g of organic phase, with the aqueous phase discarded. The wet cake is recovered from the filter and added to a 1-liter glass beaker along with deionized water (250 g) then heated to 100° C. concurrent with magnetic stirring. After 1 minute at 100° C., the stirred slurry is filtered while hot through a coarse-fritted glass filter. The crystalline product cake is packed, then washed on the filter with boiling deionized water (100 g). The product recovered from the filter is dried in a vacuum oven at 80° C. and 1 mm Hg to a constant weight of 78.9 g of white crystalline product. HPLC analysis using a uv detector set at 220 nm of a portion of the crystalline product provides the following distribution of components in their relative order of elution (Table X). The data is unnormalized with respect to unknowns and impurities in the HPLC solvents and on the HPLC column.

TABLE X

FINAL CRYSTALLINE PRODUCT: FIFTH PRODUCT

| Compound | Area percent |
|---|---|
| phenol | 0.45 |
| 1,2,2-tris(4-hydroxyphenyl)propane | 0.52 |
| trans-4,4'-dihydroxy-α-methylstilbene | 86.47 |
| 2,3-bis(4-hydroxyphenyl)propene | 0.04 |
| dimer I | 4.64 |
| cis-4,4'-dihydroxy-α-methylstilbene | 3.98 |
| dimer II | 0.68 |

Analysis of a portion of the (unstripped) organic phase for water is completed by externally standardized gas chromatography using a thermal conductivity detector. This analysis reveals the presence of 21.51 weight percent water and 73.89 weight percent phenol, with 4.6 weight percent remaining by difference for all other components including chloroacetone. The amount of phenol recovered in the organic phase represents 79.4 weight percent of the initial phenol used in the reaction.

In summary, each reaction in the series is ran using essentially the same experimental conditions, including 15:1:1 phenol:chloroacetone:sulfuric acid molar stoichiometry, 84.9+/−2.4 percent chloroacetone conversion in the condensation reaction and dehydrochlorination reaction at 80° C. in aqueous media. Because of these relatively constant experimental conditions, sequential recycle of stripped organic phase is the only variable which changes, thus the results clearly show the effect of this single variable.

The recovered crystalline product weights from these reactions are collectively given in Table XI as a function of the specific recycle reaction.

TABLE XI

CRYSTALLINE PRODUCT WEIGHT AS A FUNCTION OF RECYCLE REACTION

| Reaction Designation | Crystalline Product Weight (grams) | Percent of Initial Reaction |
|---|---|---|
| 1 (initial) | 40.9 | |
| 2 (1st recycle) | 67.6 | 165 |
| 3 (2nd recycle) | 94.4 | 231 |
| 4 (3rd recycle) | 82.6 | 202 |
| 5 (4th recycle) | 78.9 | 193 |

It is not possible to calculate the yield of isolated 4,4'-dihydroxy-α-methylstilbene for any of the reactions other than the initial reaction, because the amount of 4,4'-dihydroxy-α-methylstilbene contained in the recycled stripped organic phase is only known on an area percent, and not weight percent, basis. However, the data clearly indicate substantial gains in the recovery of crystalline product on a weight basis, with a maximum recovery in the third reaction (second recycle) of 231 percent that of the initial reaction (no recycle). A decline in recovery of crystalline product occurs in the fourth reaction (3rd recycle) to provide double that of the initial reaction, or 202 percent, with only a slight decline thereafter in the fifth (4th recycle) reaction.

The purity of the recovered crystalline product from these reactions is collectively given in Table XII as a function of the specific recycle reaction.

TABLE XII

CRYSTALLINE PRODUCT PURITY AS A FUNCTION OF RECYCLE REACTION

| | Reaction Designation | | | | |
|---|---|---|---|---|---|
| Component | 1 (initial) | 2 (1st recycle) | 3 (2nd recycle) | 4 (3rd recycle) | 5 (4th recycle) |
| trans-4,4'-dihydroxy-α-methylstilbene | 91.33 | 91.59 | 90.29 | 91.17 | 86.47 |
| cis-4,4'-dihydroxy-α-methylstilbene | 1.67 | 3.80 | 2.52 | 1.39 | 3.98 |
| 2,3-bis(4-hydroxyphenyl)propene | 2.41 | 0.32 | 0.68 | 0.30 | 0.04 |
| Total trans- plus cis-4,4'-dihydroxy-α-methylstilbene | 93.0 | 95.4 | 92.8 | 92.6 | 90.5 |
| Total Diphenols | 95.4 | 95.7 | 93.5 | 92.9 | 90.5 |

TABLE XII-continued

CRYSTALLINE PRODUCT PURITY AS A FUNCTION OF RECYCLE REACTION

| | Reaction Designation | | | | |
|---|---|---|---|---|---|
| Component | 1 (initial) | 2 (1st recycle) | 3 (2nd recycle) | 4 (3rd recycle) | 5 (4th recycle) |
| 1,2,2-tris(4-hydroxyphenyl)propane | 0.15 | trace | 0.17 | 0.67 | 0.52 |
| dimer I | 1.68 | 2.14 | 2.67 | 2.69 | 4.64 |
| dimer II | 0.08 | 0.13 | 0.29 | 0.47 | 0.68 |
| Total Tetraphenols | 1.76 | 2.27 | 2.96 | 3.16 | 5.32 |

The data clearly demonstrate a progressive decrease in total diphenol content of the crystalline product as a function of increasing recycle, from 95.4 area percent in the initial reaction to 90.5 area percent in the final reaction (4th recycle). However, decrease in the desired product, trans-4, 4'-dihydroxy-α-methylstilbene (or trans- plus cis-4,4'-dihydroxy-α-methylstilbene), does not occur until the final reaction (4th recycle). The decrease in diphenol content in the crystalline product is accompanied by the expected increase in trisphenol and tetraphenolic coproducts. With regard to the trisphenolic coproduct, a minor, relatively constant amount is present in the first, second and third reactions (initial through 2nd recycle) with a significant increase in the fourth reaction (3rd recycle) which remains relatively constant in the fifth reaction (4th recycle). By way of contrast, the tetraphenolic dimer content increases throughout the series of reactions, with the increase between the fourth and fifth reactions being of the greatest magnitude.

As previously documented herein, visual appearance of the first crystalline precipitate in the organic phase during the removal of phenol via rotary evaporation is used as the endpoint for the rotary evaporations. Analytical data for the stripped organic phase used in these recycle reactions are collectively given in Table XIII as a function of the specific recycle reaction.

TABLE XIII

STRIPPED ORGANIC PHASE AS A FUNCTION OF RECYCLE REACTION

| | Reaction Designation | | | |
|---|---|---|---|---|
| | 2 (1st recycle) | 3 (2nd recycle) | 4 (3rd recycle) | 5 (4th recycle) |
| Stripped organic phase weight (grams) | 213.9 | 217.3 | 247.8 | 276.6 |
| Actual weight of stripped organic phase recycled (grams) | 207.5 | 199.09 | 247.8 | 276.6 |
| Increase in recyclable organic phase as a percent of 1st recycle | | 101.6 | 115.9 | 129.3 |
| Phenol recovered in distillate as a percent of phenol used in the condensation reaction | 44.5 | 52.5 | 54.6 | 56.9 |
| Phenol in stripped organic phase (area %) | 31.4 | 18.3 | ND | 12.7 |
| 4,4'-Dihydroxy-α-methylstilbene in stripped organic phase (area %) | 44.1 | 42.2 | ND | 38.1 |

The data clearly demonstrate a progressive increase in the amount of total stripped organic phase as a function of increasing recycle. Thus, from reaction 2, the 1st recycle, to reaction 5, the 4th recycle, a 129.3 percent increase in weight of the stripped organic phase occurs. This weight increase is a direct result of coproducts concentrating in the stripped organic phase with progressive recycle. It is notable that between reaction 2 (1 st recycle) and reaction 3 (2nd recycle), only a very minor increase in weight of the stripped organic phase occurs to 101.6 percent. As previously documented herein and also shown in Table XIII, in reaction 2 (1st recycle) and reaction 3 (2nd recycle), not all of the stripped organic phase produced is recycled. It would be possible to normalize the data given to reflect changes expected from recycle of these additional amounts, however, because of their small size, this is not deemed to be necessary. The HPLC analysis shows a substantial progressive decrease in phenol concentration as a function of increasing recycle. Stated in a different way, more phenol must be stripped from the organic phase as the buildup of coproducts occurs in this phase through the recycle process. Without removal of this additional phenol, the indicator for termination of the rotary evaporation, appearance the first crystalline precipitate in the organic phase during the removal of phenol, would not occur. In fact, the gas chromatographic analyses for phenol recovered in the distillate, shown in Table XIII as a percent of the phenol used in the original condensation reaction, quantifies the removal of additional phenol as a function of progressive recycle. The HPLC analysis also shows a slow progressive decrease in 4,4'-dihydroxy-α-methylstilbene concentration as a function of progressive recycle. This decrease is a direct result of dilution via the buildup of coproducts as a function of increasing recycle.

The experiments employing recycle of stripped organic phase into the crystalline slurry formation step are successful in providing more than double (231 percent) the recovery of crystalline product after only 2 recycles. A slight decline (to 193 percent) in recovery by the fifth reaction (4th recycle) is attributed to the observed buildup of coproducts in the stripped organic phase which solubilize more of the 4,4'-dihydroxy-α-methylstilbene, thus hindering its recovery into the crystalline product. While this occurs as a function of progressive recycle, it is countered to some extent by increasing the amount of phenol stripped from the organic phase. Excellent purity of the crystalline product is maintained throughout the entire sequence of recycle reactions, with collective trans- plus cis-4,4'-dihydroxy-α-methylstilbene content exceeding 90 area percent. In fact, for the first 4 reactions (initial through 3rd recycle), collective trans- plus cis-4,4'-dihydroxy-α-methylstilbene content remained at a constant 93 area percent. The partitioning of coproducts into the crystalline product increases as a function of progressive recycle but with different behaviors depending on the specific coproduct. Thus, the trisphenol, 1,2,2-tris(4-hydroxyphenyl)propane, favors partitioning into the organic phase until a critical concentration builds in said phase at the fourth reaction (3rd recycle). By way of contrast, the tetraphenolic dimers (dimer I and dimer II) consistently increase in the crystalline product as a function of progressive recycle. These differences may be explained by the molecular association of the rodlike α-methylstilbene mesogen of trans-4,4'-dihydroxy-α-methylstilbene, which structurally predominates the crystalline product, with the rodlike α-methylstilbene mesogen present as a part of the structure of dimer I. Conversely, the non-mesogenic and non-rodlike trisphenol has no structural features favoring molecular association with the trans-4,4'-dihydroxy-α-methylstilbene, and thus prefers to remain solubilized in the phenol and coproduct rich organic phase.

What is claimed is:

1. A process for preparing a 4,4'-dihydroxy-alpha-alkylstilbene or 4,4'-dihydroxy-alpha,alpha'-dialkylstilbene which comprises:

(A) reacting at a temperature of from −20° C. to 20° C. a mixture of:

(1) at least one alpha-haloketone;

(2) at least one compound containing one phenolic hydroxyl group or aromatic alkoxy group per molecule such that the mole ratio of phenolic hydroxyl group-containing or aromatic alkoxy group-containing compound(s):alpha-haloketone(s) is at least 0.1:1; and (3) either (a) at least one strong protonic acid or (b) at least one Lewis acid, or (c) any combination thereof; such that the mole ratio of phenolic hydroxyl group-containing or aromatic alkoxy group-containing compound(s):alpha-haloketone(s):strong protonic acid(s) or Lewis acid(s) or combination thereof is from 0.1:1:0.0026 to 20:1:8; thereby forming a reaction product containing at least one halogen-containing bisphenol compound which, upon being dehydrohalogenated, forms a 4,4'-dihydroxy-alpha-alkylstilbene or 4,4'-dihydroxy-alpha,alpha'-dialkylstilbene;

(B) reducing the acid content of the product resulting from step (A) to less than 10,000 ppm;

(C) dehydrohalogenating the product obtained from step (B), thereby forming a dehydrohalogenated product containing 4,4'-dihydroxy-alpha-alkylstilbene or 4,4'-dihydroxy-alpha,alpha'-dialkylstilbene;

(D) adding water to the product of step (C) in amounts sufficient to crystallize at least a portion of the 4,4'-dihydroxy-alpha-alkylstilbene or 4,4'-dihydroxy-alpha,alpha'-dialkylstilbene and recovering the crystals and the remaining organic phase separately;

(E) independently repeating steps (A), (B), and (C) to obtain a dehydrohalogenated product;

(F) mixing at least a portion of organic phase obtained in step (D) with the product obtained in step (E); and (G) adding mater to the mixture obtained in step (F) in amounts sufficient to crystallize at least a portion of the 4,4'-dihydroxy-alpha-alkylstilbene or 4,4'-dihydroxy-alpha,alpha'-dialkylstilbene and recovering the crystals.

2. The process of claim 1 wherein step (A) comprises reacting a temperature of from −15° C. to +10° C. a mixture of:

(1) chloroacetone;

(2) phenol in amounts such that the mole ratio of phenol:chloroacetone 2.1:1 to 15:1;

(3) sulfuric acid or methanesulfonic acid, such that the mole ratio of phenol:chloroacetone:sulfuric acid or methanesulfonic acid is in the range of from 2.1:1:1 to 15:1:4; and (4) optionally, methylene chloride.

3. The process of claim 2 wherein step (A) is carried out at a temperature of from −13° C. to 0° C. and in the presence of methylene chloride.

4. The process of claim 1 wherein the organic phase used in (F) has been stripped by distillation to remove at least 20 percent by weight of the phenolic hydroxyl group-containing compound or aromatic alkoxy group-containing compound.

5. The process of claim 4 wherein the organic phase used in (F) has been stripped by distillation to remove at least 80 percent of the phenolic hydroxyl group-containing compound or aromatic alkoxy group-containing compound.

6. The process of claim 5 wherein the organic phase used in (F) has been stripped by distillation to remove the phenolic hydroxyl group-containing compound or aromatic alkoxy group-containing compound.

7. The process of claim 4 wherein the phenolic hydroxyl group-containing compound removed by distillation is used as a reactant in step (A)(2).

8. The process of claim 4 wherein a basic-acting compound is added to the organic phase prior to stripping via distillation.

9. The process of claim 8 wherein the basic-acting compound is sodium bicarbonate.

10. The process of claim 4 wherein said organic phase is additionally subjected to thermal, catalytic or thermocatalytic conditions which dedimerize all or a part of the dimeric coproducts contained in said organic phase prior to recycle.

11. A process for preparing a 4,4'-dihydroxy-alpha-alkylstilbene or 4,4'-dihydroxy-alpha,alpha'-dialkylstilbene which comprises:

(A) reacting at a temperature of from −20° C. to 20° C. a mixture of:

(1) at least one alpha-haloketone;

(2) at least one compound containing one phenolic hydroxyl group or aromatic alkoxy group per molecule such that the mole ratio of phenolic hydroxyl group-containing or aromatic alkoxy group-containing compound(s):alpha-haloketone(s) is at least 0.1:1; and (3) either (a) at least one strong protonic acid or (b) at least one Lewis acid, or (c) any combination thereof; such that the mole ratio of phenolic hydroxyl group-containing or aromatic alkoxy group-containing compound(s):alpha-haloketone(s):strong protonic acid(s) or Lewis acid(s) or combination thereof is from 0.1:1:0.0026 to 20:1:8; thereby forming a reaction product containing at least one halogen-containing bisphenol compound which, upon being dehydrohalogenated, forms a 4,4'-dihydroxy-alpha-alkylstilbene or 4,4'-dihydroxy-alpha,alpha'-dialkylstilbene;

(B) reducing the acid content of the product resulting from step (A) to less than 10,000 ppm;

(C) dehydrohalogenating the product obtained from step (B), thereby forming a dehydrohalogenated product containing 4,4'-dihydroxy-alpha-alkylstilbene or 4,4'-dihydroxy-alpha,alpha'-dialkylstilbene;

(D) adding water to the product of step (C) in amounts sufficient to crystallize at least a portion of the 4,4'-dihydroxy-alpha-alkylstilbene or 4,4'-dihydroxy-alpha,alpha'-dialkylstilbene;

(E) recovering the crystals and the remaining organic phase separately;

(F) independently repeating steps (A), (B), (C), and (D) to obtain an aqueous slurry containing crystallized 4,4'- dihydroxy-alpha-alkylstilbene or 4,4'-dihydroxy-alpha,alpha'-dialkylstilbene;

mixing at least a portion of the organic phase obtained in step (D) with the slurry obtained in step (F) under conditions sufficient to crystallize at least a portion of the 4,4'-dihydroxy-alpha-alkylstilbene or 4,4'-dihydroxy-alpha,alpha'-dialkylstilbene present in the organic phase obtained in step (D); and recovering the crystals of 4,4'-dihydroxy-alpha-alkylstilbene or 4,4'-dihydroxy-alpha,alpha'-dialkylstilbene.

12. The process of claim 11 wherein step (A) comprises reacting a temperature of from −15° C. to +10° C. a mixture of:

(1) chloroacetone;

(2) phenol in amounts such that the mole ratio of phenol:chloroacetone 2.1:1 to 15:1;

(3) sulfuric acid or methanesulfonic acid, such that the mole ratio of phenol:chloroacetone:sulfuric acid or methanesulfonic acid is in the range of from 2.1:1:1 to 15:1:4; and (4) optionally, methylene chloride.

13. The process of claim 12 wherein step (A) is carried out at a temperature of from −13° C. to 0° C. and in the presence of methylene chloride.

14. The process of claim 11 wherein the organic phase used in (F) has been stripped by distillation to remove at least 20 percent by weight of the phenolic hydroxyl group-containing compound or aromatic alkoxy group-containing compound.

15. The process of claim 14 wherein the organic phase used in (F) has been stripped by distillation to remove at least 80 percent of the phenolic hydroxyl group-containing compound or aromatic alkoxy group-containing compound.

16. The process of claim 15 wherein the organic phase used in (F) has been stripped by distillation to remove the phenolic hydroxyl group-containing compound or aromatic alkoxy group-containing compound.

17. The process of claim 14 wherein the phenolic hydroxyl group-containing compound removed by distillation is used as a reactant in step (A)(2).

18. The process of claim 14 wherein a basic-acting compound is added to the organic phase prior to stripping via distillation.

19. The process of claim 18 wherein the basic-acting compound is sodium bicarbonate.

20. The process of claim 14 wherein said organic phase is additionally subjected to thermal, catalytic or thermocatalytic conditions which dedimerize all or a part of the dimeric coproducts contained in said organic phase prior to recycle.

* * * * *